(12) United States Patent
Caruso et al.

(10) Patent No.: US 7,541,036 B2
(45) Date of Patent: Jun. 2, 2009

(54) HUMAN IMMUNODEFICIENCY VIRUS TYPE 1 (HIV-1) MATRIX (MA OR P17) POLYPEPTIDE CAPABLE OF INDUCING ANTI-P17 ANTIBODIES THAT NEUTRALIZE THE PROINFLAMMATORY ACTIVITIES OF THE MA PROTEIN

(75) Inventors: Arnaldo Caruso, Brescia (IT); Jose Sebastian Franzone, Turin (IT)

(73) Assignee: Medestea Internazionale S.r.l., Torino (IT)

( * ) Notice: Subject to any disclaimer, the term of this patent is extended or adjusted under 35 U.S.C. 154(b) by 492 days.

(21) Appl. No.: 10/485,980

(22) PCT Filed: Aug. 5, 2002

(86) PCT No.: PCT/IB02/03093

§ 371 (c)(1),
(2), (4) Date: Jul. 30, 2004

(87) PCT Pub. No.: WO03/016337

PCT Pub. Date: Feb. 27, 2003

(65) Prior Publication Data

US 2004/0249124 A1 Dec. 9, 2004

(30) Foreign Application Priority Data

Aug. 7, 2001 (IT) ............................ TO2001A0795
Nov. 2, 2001 (IT) ............................ TO2001A1042

(51) Int. Cl.
*A61K 39/21* (2006.01)
*A61K 39/385* (2006.01)

(52) U.S. Cl. .............................. 424/188.1; 424/196.11; 424/208.1

(58) Field of Classification Search ........................ None
See application file for complete search history.

(56) References Cited

U.S. PATENT DOCUMENTS 6,268,472 B1 7/2001 Zimmerman et al.

FOREIGN PATENT DOCUMENTS

EP 0 426 314 5/1991
EP 0 620 009 10/1994
EP 0 620 009 A1 * 10/1994

OTHER PUBLICATIONS

Ghose, A. C., and F. Karush, 1988, "Induction of polyclonal and monoclonal antibody responses to cholera toxin by the synthetic peptide approach", Mol. Immunol. 25(3):223-230 (abstract provided).*
Gorse, G. J., et al., 1996, "A dose-ranging study of a prototype synthetic HIV-1MN branched peptide vaccine", J. Infect. Dis. 173(2):330-339 (abstract provided).*
Burton, D. R., and J. P. Moore, 1998, "Why do we not have an HIV vaccine and how can we make one?", Nat. Med. Vac. Suppl. 4(5):495-498.*
Moore, J. P., and D. R. Burton, 1999, "HIV-1 neutralizing antiobodies: How full is the bottle?", Nat. Med.5(2):141-144.*
McMichael, A. J., and T. Hanke, 2003, "HIV vaccines 1983-2003", Nat. Med. 9(7):874-880.*
Desrosiers, R.C., 2004, "Prospects for an AIDS vaccine", Nat. Med. 10(3):221-223.*
Haigwood, N. L., 2004, "Predictive value of primate models for AIDS", AIDS Rev. 6:187-198.*
Gallo, R. C., 2005, "The end or the begining of the drive to an HIV-positive vaccine: a view from over 20 years", Lancet 366:1894-1898.*
Buratti et al. "A neutralizing monoclonal antibody previously mapped exclusively on human immunodeficiency virus type 1 gp41 recognizes an epitope in p17 sharing the core sequence IEEE" Journal of Virology, vol. 71, No. 3, 1997 pp. 2457-2462.

* cited by examiner

*Primary Examiner*—Jeffrey S. Parkin
(74) *Attorney, Agent, or Firm*—Merchant & Gould P.C.

(57) ABSTRACT

New isolated polypeptides of the protein p17 of HIV are described, represented by the formula: $NH_2$-$X^1$-Gly-$X^2$-$X^3$-Leu-Asp-$X^4$-Trp-Glu-$X^5$-Ile-$X^6$-Leu-Arg-COOH (SEQ ID NO:1) in which $X^1$ is an amino acid residue selected from Ser and Arg; $X^2$ is an amino acid residue selected from Gly, Glu and Ser; $X^3$ is an amino acid residue selected from Glu, Lys, Asp and Arg; $X^4$ is an amino acid residue selected from Arg, Ala, Lys, Thr, Ser, Glu, Asp and Gln; $X^5$ is an amino acid residue selected from Lys, Arg and Ser; and $X^6$ is an amino acid residue selected from Arg and Gln. These polypeptides, when administered to a subject, are able to evoke anti-p17 neutralizing antibodies and are therefore useful as vaccine or inoculum. Monoclonal and polycolonal anti-p17 antibodies which are able to neutralize the biological activity of this viral protein and to recognize its neutralization epitope in a specific manner are also described.

8 Claims, No Drawings

HUMAN IMMUNODEFICIENCY VIRUS TYPE 1 (HIV-1) MATRIX (MA OR P17) POLYPEPTIDE CAPABLE OF INDUCING ANTI-P17 ANTIBODIES THAT NEUTRALIZE THE PROINFLAMMATORY ACTIVITIES OF THE MA PROTEIN

The present invention relates to isolated polypeptides based on a sequence of the amino terminal region of the p17 protein of HIV, useful in therapy and in the diagnosis of the human acquired immune deficiency syndrome (AIDS), as well as to anti-p17 neutralizing antibodies which specifically recognize this amino terminal sequence.

AIDS comprises a group of clinical syndromes caused by a retro virus called the human immune deficiency virus (HIV). HIV infects in a preferential manner the cells which express the antigen CD4 on their surface, thus the helper T-lymphocytes and the macrophages, but also the dendritic cells of the lymph nodes.

Infection by HIV can be blocked in vitro by means of antibodies obtained from the serum of infected individuals.

Over the course of the years various HIV neutralizing antibodies have been developed, most of which react with the protein products of the env gene.

These protein products have been utilized as immunogens in various forms, for example as glycoprotein extracts, recombinant proteins and synthetic peptides.

The products of env have been traditionally considered the most immunogenic proteins of HIV and most suitable to stimulate a protective immune response against HIV.

However, researchers have turned their attention also to the proteins encoded by other genes of HIV, for example those of gag. The gene gag, as is known, encodes a precursor polyprotein having a molecular weight of about 55,000 (p55), which is cut by the protease of pol into the polypeptides p24, p17 and p15 which constitute the structural proteins of the core of the virion.

Some studies have indicated that the products of the gag gene can be the target of a neutralizing immune response.

In particular it has been disclosed that the p17 protein of HIV can be the target of antibodies neutralizing the replication of HIV and that high levels of anti-p17 antibodies are correlated with a slower progression of AIDS.

U.S. Pat. No. 5,185,147 presents several isolated polypeptide sequences based on the aminoterminal region of p17, described as being able to evoke anti-p17 antibodies which interact with the viral particle of HIV by modifying the infecting capacity in vitro. However, as is known from electron microscope studies (for example Andreassen, H., H. Bohr, J. Bohr, S. Brunak, T. Bugge, R. M. J. Cotterill, C. Jacobsen, P. Kush, B. Lautrup, S. B. Petersen, T. Saemark, and K. Ulrich, 1990, J. Acquir. Immune Def. Syndr. 3:615-622) the p17 protein is located within the viral particle and therefore is not available to the interaction with anti-p17 antibodies. The modification of the in vitro infecting capacity of the viral particle of HIV observed in this study is therefore not ascribable to an effective inhibition of the biological activity of the protein p17.

The problem which the present invention addresses is that of finding polypeptides based on the sequence of the p17 protein which will be effectively able to evoke antibodies neutralizing the biological activity of the p17 protein of HIV.

To solve this problem the present inventors have first of all studied the mechanisms by which the protein p17 exercises its biological effects.

As will be described in more detail in the section relating to the examples, they have found that the biological activity of p17 derives on the one hand from its capacity to increase the production of pro-inflammatory cytokines having pro-HIV action, such as IFN-γ and TNF-α, and on the other hand from its capacity to increase the production of these pro-inflammatory cytokines when this is inhibited by anti-inflammatory cytokine, such as for example IL-4.

Moreover, the present inventors have found that the biological activity of the protein p17 develops through an interaction between the protein in the form of a distinct entity, separated from the viral particle, and specific receptors expressed on the surface of the HIV target cell. The existence of these p17 receptors on lymphocytes which are the target of HIV has not until now been suggested.

The present invention is based upon the discovery of the p17/receptor interaction.

By studying the p17/receptor interaction the inventors have in fact identified a region of the p17 protein which constitutes the region that binds to the cell receptor and that is able to elicit antibodies inhibiting the biological activity of the p17 protein, as well as its binding to the receptor itself. In the present description these antibodies will be indicated as "anti-p17 neutralizing antibodies" and, where appropriate, this binding region will be indicated as the "neutralizing epitope".

The inventors have therefore verified that isolated polypeptides, having an amino acid sequence based on that of the neutralizing epitope of p17 protein, that is the sequence in the N-terminal region lying between the amino acid positions 9 and 22 of p17, solve the problem addressed by the present invention since, thanks to their secondary structure, such polypeptides are able to evoke antibodies neutralizing the biological activity of the protein p17. Such polypeptides are therefore particularly suitable for use in a vaccine for interfering with the replication of HIV.

The numbering of the amino acids residues of the p17 sequence utilized here is in accordance with that proposed in Ratner et al (1985), Nature 313:277.

Moreover, it has been demonstrated that the polypeptides of the invention are specifically recognized by neutralizing anti-p17 monoclonal antibodies, whilst they are not recognized by non-neutralizing anti-p17 monoclonal antibodies. Such polypeptides are therefore particularly suitable also for use in diagnostic methods to detect the presence of anti-p17 neutralizing antibodies in a subject infected with HIV, as well as in methods for the purification of such antibodies.

A first object of the invention is therefore an isolated polypeptide capable of reacting specifically with a neutralizing antibody anti-p17 of HIV, having an amino acid sequence which corresponds to the neutralizing epitope of the protein p17 of HIV, that is to say the sequence lying between position 9 and position 22 of the protein p17 of HIV.

As will be described in more detail in the examples, the inventors have initially constructed a synthetic polypeptide as defined above, based on the sequence of the neutralizing epitope of the protein p17 contained in the plasmid BH10 (laboratory stock). This synthetic polypeptide has the sequence NH$_2$-Ser-Gly-Gly-Glu-Leu-Asp-Arg-Trp-Glu-Lys-Ile-Arg-Leu-Arg-COOH (SEQ ID NO: 2). The inventors have verified experimentally that this polypeptide is specifically recognized by neutralizing monoclonal antibodies obtained against p17 of BH10.

This polypeptide is therefore suitable for use as an immunogen able to elicit antibodies neutralizing the biological activity of p17 of BH10.

It has further been verified that variants of the protein p17 characteristic of other strains of HIV have changes in the region of the neutralizing epitope which, however, do not significantly alter their recognition by antibodies neutralizing the biological activity of the p17. Among these variants we cite, by way of illustrative example, the sequences of the p17 of viral strains prevalent in Africa (clade C).

Isolated polypeptides having an amino acid sequence based on the sequence lying between positions 9 and 22 of the protein p17 of the viral strains prevalent in specific geographical areas therefore make it possible to obtain antibodies having greater affinity in comparison with the corresponding protein p17 and therefore lend themselves particularly for use as vaccines to use in these geographical areas.

By using the information of sequences contained in the genetic data banks (for example GenBank) relating to the sequence of p17 of strains coming from different geographical areas, the present inventors have therefore obtained a series of synthetic polypeptides corresponding to the positions 9 to 22 of the p17 of different strains of HIV, which share the immunological property of reacting specifically with neutralizing antibodies directed against p17 of the corresponding strain of HIV.

These polypeptides are represented by the general formula: $NH_2$-$X^1$-Gly-$X^2$-$X^3$-Leu-Asp-$X^4$-Trp-Glu-$X^5$-Ile-$X^6$-Leu-Arg-COOH (SEQ ID NO: 1) in which $X^1$ is an amino acid residue selected from Ser and Arg; $X^2$ is an amino acid residue selected from Gly, Glu and Ser; $X^3$ is an amino acid residue selected from Glu, Lys, Asp and Arg; $X^4$ is an amino acid residue selected from Arg, Ala, Lys, Thr, Ser, Glu, Asp and Gln; $X^5$ is an amino acid residue selected from Lys, Arg and Ser; and $X^6$ is an amino acid residue selected from Arg and Gln.

All the amino acids identified in the present description are in the L-configuration. The abbreviations utilized for the amino acid residues are in accordance with the standard nomenclature.

Within the group of polypeptides described above, the polypeptide having the amino acid sequence $NH_2$-Ser-Gly-Gly-Glu-Leu-Asp-Arg-Trp-Glu-Lys-Ile-Arg-Leu-Arg-COOH (SEQ ID NO: 2) constitutes the preferred embodiment. This polypeptide corresponds to the sequence between positions 9 and 22 of p17 of the laboratory strain BH10 of HIV-1, which is representative of strains existing in Europe and America (clade B).

For the purpose of increasing solubility, the polypeptides of the invention can be bound to a second amino acid sequence suitable for this purpose, such as, for example, the sequence -Pro-Gly-Gly-Lys-Lys-Lys-Tyr-Lys-COOH (SEQ ID NO: 3), which corresponds to the positions 23 to 30 of the protein p17 of the strain HB10 of HIV-1.

In this embodiment, the second amino acid sequence is bound directly to the carboxyterminal residue of the polypeptide according to the invention.

The polypeptides of the invention have the capability of evoking a neutralizing immune response when administered to a patient infected by the corresponding strain of HIV, and are therefore suitable for use in a vaccine.

Within the present description, the term vaccine is intended to include a composition comprising a polypeptide according to the invention as the active ingredient and a pharmaceutically acceptable vehicle, such composition being capable of inducing active immunity in a subject—for example a mammal, including a human being—to which it is administered in an effective quantity.

A second object of the invention is therefore a vaccine composition comprising a polypeptide of the invention and a pharmaceutically acceptable vehicle. Such a composition is also suitable to be utilized as inoculum to be administered to a non-human mammal to generate antibodies which immunoreact with HIV, in particular neutralizing anti-p17 antibodies of HIV.

In a preferred embodiment, when the polypeptides are utilized in a vaccine or inoculum composition, the polypeptides can be conjugated with a suitable carrier molecule, that is to say a molecule able to couple with the polypeptide and render it immunogenic. A polypeptide as defined above, which is conjugated with a carrier, therefore falls within the scope of the present invention.

Examples of carriers suitable for this purpose are proteins such as KLH ("keyhole limpet haemocyanin"), edestin, thyroglobulin, albumins such as bovine serum albumin (BSA) or the human serum albumin (HSA), erythrocytes such as sheep erythrocytes (SRBC), tetanus anatoxin, cholera anatoxin, polyamino acids such as, for example, poly (D-lysine: D-glutamic acid) and the like.

To facilitate the binding of the polypeptide to the carrier molecule amino acid residues can be added to the N-terminus or to the C-terminus of the polypeptide. The use of an additional residue of cysteine (Cys) to the C-terminus of the polypeptide is particularly suitable for this purpose, since—as is known—cysteine is able to form disulphide bridges.

Consequently, when the polypeptide of the invention is to be conjugated to a carrier, it preferably contains an additional residue of cysteine (Cys) bound to the carboxyterminal residue of the polypeptide. In this context, the expression carboxyterminal residue of the polypeptide is intended to mean either the carboxyterminal residue of the sequence that constitutes the neutralizing epitope of p17 (Arg 22 in SEQ ID NO: 1 or SEQ ID NO: 2) or the carboxyterminal residue of the second amino acid sequence having the function of increasing the solubility of the polypeptide (Lys 30 in SEQ ID NO. 3).

Moreover, in another embodiment, the polypeptide can contain also an additional residue of norleucine (Nleu) in the C-terminal position which precedes the additional cysteine residue mentioned above, for a greater traceability of the peptide during the processes of conjugation with the carrier molecule.

Therefore, in an embodiment of the invention, the polypeptide is conjugated with a carrier, preferably through an additional residue of cysteine (Cys) or an additional Nleu-Cys dipeptide in the carboxyterminal position.

As an alternative to the use of a carrier, the polypeptides of the invention can be used in the form of branched peptides.

A polypeptide as previously defined, in the form of a branched peptide also falls therefore within the scope of the present invention.

The expression "branched peptide" is intended to indicate a complex having a high molecular weight constituted by a plurality of identical copies of a polypeptide of the invention bound to a central core which is able to simultaneously bind a plurality of identical copies of the said polypeptide.

A branched peptide can be obtained by binding the polypeptide in several copies to a central core of polylysine "MAP technology", in such a way as to achieve a high molecular weight and to be immunogenic even without the presence of the carrier molecule (Nordelly B., et el., 1992, J. Immunol. 148: 914-920). The core of polylysine may moreover be modified as described for example in Okeda K., et el., 1993, Journal of Molecular Recognition 6:101-109 or substituted by other substances, such as, for example, glucose which has the same capacity as polylysine of binding several molecules of the same polypeptide and therefore generating complexes having high molecular weight.

The choice of the carrier or of the type of core is based on known criteria and is substantially independent of the epitope utilized, so it does not form a specific subject of the present invention and therefore will not be discussed in greater detail.

The vaccine or inoculum composition of the invention may moreover contain further ingredients including, for example, an antigenic adjuvant, that is to say a substance able to increase the efficacy or immunogenicity of an antigen.

Since some of the adjuvants suitable for animals are not suitable for humans, the adjuvants of the vaccine and of the inoculum may be the same or different.

As adjuvants useable in a vaccine we list by way of illustrative example, Alum (aluminium hydroxide), the incomplete Freund's adjuvant, and the compound MF59 recently described by Graham B. S., et al. (Ann. Int. Med. 1996, 125:270-279).

The vaccine or inoculum of the present invention contains an effective quantity of a polypeptide of the invention. The effective quantity of polypeptide per unitary dose depends on criteria, however well known, which include, among other things, the species to which the subject to be inoculated belongs, the body weight of the subject to be inoculated and the predetermined administration regime. The vaccines and inocula typically contain quantities of polypeptide which can vary from 1 to 100 micrograms/kg for use in mammals of average size (goats, dogs, monkeys) and in man, and from about 10 mg to about 500 micrograms per dose in small animals (mice, rats, rabbits, hamsters).

These quantities are based on the weight of polypeptide as such, without taking account of the weight of the carrier when this is utilized.

As indicated above, the polypeptides of the invention can be used as specific reagents in an assay for detecting the presence in a sample of a biological material of anti-p17 neutralizing antibodies, that is to say antibodies which are directed against the protein p17 and which are able to neutralize the biological activity of the said protein.

This assay may for example be utilized for monitoring the anti-viral and immunomodulation therapies and for monitoring the progression of the HIV infection.

This assay can also be utilized for industrial applications, for example for control of the quality of anti-p17 immunoglobin preparations obtained by means of chromatography or other preparative methodologies.

The assay for the detection of anti-p17 neutralising antibodies can be an immunological assay, such as, for example, an immunoenzymatic assay in heterogeneous phase (ELISA, enzyme-linked immunosorbent technique) or in homogeneous phase (EMIT, enzyme multiplied immuno technique), a radioimmunological assay, an immunological assay based on the fluorescence, a Western blot assay, or any other technique in which the antibody or antigen is marked with a detectable molecule or with any other indicator means.

An isolated polypeptide based on the neutralizing epitope of p17 according to the invention or a mixture of such polypeptides can be utilized as the antigen. The polypeptide can optionally be conjugated with a carrier molecule for the purpose of facilitating its binding to a support or to increase the molecular weight for a better recognition in Western blotting analyses.

For example in an immunoenzymatic ELISA test, a polypeptide according to the invention utilized as the antigen can be coated on a solid support, such as, for example, a microtitration plate, a strip, or a well, using methods known in the art.

The antigen bound to the solid support is then incubated with a sample of the biological material of interest, that is to say the material within which it is desired to verify the presence of anti-p17 neutralising antibodies.

This biological material can be, for example, plasma, serum, cerebrospinal fluid, urine, saliva, or a cell culture or tissue culture fluid and the like.

The bound antibody can be detected by the addition of an antiserum or a monoclonal antibody conjugated with an enzyme. For this purpose any enzymatic label known in the art can be utilized (for example horseradish peroxidase, alkaline phosphatase, etc). The sensitivity of the test can be further improved with the use of a biotin-avidin or streptavidin system for the detection of the analyte.

The final detection can be obtained by the addition of a solution of substrate, which varies depending upon the enzyme utilized. Examples of suitable substrates are O-phenylene diamine, tetramethyl benzidine, paranitrophenyl phosphate.

The results can be read by eye or with a spectrophotometer. The test for the detection of anti-p17 neutralizing antibodies can be qualitative or quantitative. A quantitative test can be obtained with methodologies known in the art, for example end-point dilution or construction of a reference curve.

The polypeptides of the invention can be further utilized as specific reagents for the purification of anti-p17 neutralizing antibodies from a biological sample. Such biological sample can be a sample of a biological material taken from a subject, such as, for example, a sample of blood, plasma, serum, saliva, urine or a sample of ascitic fluid, tissue or cell culture fluid, or a preparation of immunoglobulin.

Said subject can be for example a human patient infected with the HIV virus or a non-human mammal previously inoculated with a protein capable of generating anti-p17 neutralizing antibodies. Such protein can for example be the protein p17 of HIV in a substantially purified or recombinant form, or a polypeptide derived therefrom containing at least the p17 neutralizing epitope identified in the present invention, said polypeptide being optionally conjugated with a carrier, or in the form of a branch peptide, or in any other immunogenic form.

In this context, the expression "protein p17 in a substantially purified form" is intended to indicate the protein p17 substantially isolated from the rest of the viral particle.

The neutralising antibodies can be purified with any affinity purification technique known in the art by utilizing a polypeptide according to the invention or a mixture of such polypeptides as the purification reagent.

For this purpose the polypeptide utilized as the purification reagent is bound to a matrix suitable for use in affinity purification techniques, such as, for example, agarose, silica gel, polyacrylamide, magnetic beads and the like.

The binding of the polypeptide to the matrix can be achieved by cross-linking the functional groups present on the matrix and on the peptide by interposition of a spacer arm. The spacer arms are generally $C_6$-$C_8$ aliphatic chains with functional groups able to form a bridge between the matrix and the peptide. For this purpose both hydrophobic functional groups (for example a spacer arm including a benzene ring) and hydrophilic functional groups (for example alcohols) can be used. As an alternative to the spacer arms, carrier molecules or biotin can be utilized.

To avoid denaturation of the peptide and to facilitate its binding to the matrix, it can be useful to preactivate the matrix so that subsequent binding of the ligand can be obtained under mild conditions.

The activation is a chemical reaction between the matrix and the activating compounds which lead to the formation—on the surface of the matrix itself—of reactive groups which combine promptly with ligand groups. Reactive groups such as imidocarbonate, oxirane, trichlorotriazine, O-imidazolylcarbonyl, etc are known in the art. A spacer arm with a terminal amino group can be activated by reaction with an N-hydroxysuccinamide ester or with bromoacetic acid giving a highly reactive alkylating agent.

Alternatively, the polypeptide can be bound to a matrix by means of non covalent bonds, for example by utilizing a triazine resin.

Finally, the polypeptide can be bound to a matrix by reversible covalent bonds.

Affinity linkage between the polypeptide attached to the matrix and the anti-p17 antibodies can be broken either directly, by creating conditions which discourage biospecific interactions, or by means of competitive affinity elution.

The anti-p17 antibodies that bind specifically to a polypeptide of the present invention can neutralize the biological activity of the p17 protein of HIV and interfere with the interaction between the protein and its cell receptor (see example 7).

Such antibodies can be obtained by means of the above-described purification procedure or in the form of monoclonal antibodies with the cell fusion method described in example 6.

The inventors have also verified that anti-p17 monoclonal antibodies not having the capacity to neutralize the biological activity of the protein p17 of HIV are also incapable of binding to the neutralizing epitope of p17 in an ELISA assay in solid phase (see example 8).

A further object of the present invention is therefore a monoclonal or polycolonal antibody directed against the protein p17 of HIV, which is capable of neutralizing the biological activity of the protein p17 of HIV and of specifically recognizing the neutralizing epitope of the protein p17 of HIV, said neutralizing epitope being the amino acid sequence lying between position 9 and position 22 of the p17 protein of HIV.

In a preferred embodiment the amino acid sequence of the neutralizing epitope recognized by the antibody according to the invention is the sequence: $X^1$-Gly-$X^2$-$X^3$-Leu-Asp-$X^4$-Trp-Glu-$X^5$-Ile-$X^6$-Leu-Arg- (SEQ ID NO: 1) where $X^1$ is an amino acid residue selected from among Ser and Arg; $X^2$ is an amino acid residue selected from Gly, Glu and Ser; $X^3$ is an amino acid residue selected from Glu, Lys, Asp and Arg; $X^4$ is an amino acid residue selected from Arg, Ala, Lys, Thr, Ser, Glu, Asp and Gln; $X^5$ is an amino acid residue selected from Lys, Arg and Ser; and $X^6$ is an amino acid residue selected from Arg and Gln.

More preferably, said amino acid sequence is the sequence -Ser-Gly-Gly-Glu-Leu-Asp-Arg-Trp-Glu-Lys-Ile-Arg-Leu-Arg (SEQ ID NO:2).

The antibodies of the invention can be utilized in clinical therapeutic or prophylactic applications, as specific antagonists of the protein p17 to selectively immunosuppress the physiological response induced by this viral protein and, more specifically, those responses which are involved in the up-regulation of the pro-inflammatory immune process and which are dependent upon the interaction of p17 with its cellular receptor.

Another object of the present invention is therefore the use of an antibody as defined above for the preparation of a medicament for inhibiting the immuno stimulating effects of the p17 protein of HIV produced during the course of an HIV infection.

To this end the antibodies of the invention can be used in their native form, or in a denatured form or in the form of antigen binding immunoglobulin fragments (that is to say fragments $F(Ab')_2$, Fab, Fab' or Fv). These immunoglobulin fragments can be obtained chemically, enzymatically or by means of recombinant DNA techniques, for example miniantibodies.

The antibodies or antibody fragments are preferably administered parenterally, more preferably intravenously; a slow administration is moreover greatly preferred, for example by means of a conventional intravenous administration set or from a subcutaneous depot.

When administered parenterally the antibodies are formulated in a unit of dosage in injectable form, for example a solution, an emulsion or a suspension, further comprising a pharmaceutical acceptable vehicle. The said vehicle can be aqueous or non-aqueous and, moreover, can contain substances capable of increasing the isotonicity and the chemical stability of the medicament. The antibody is preferably formulated in purified form, substantially free from aggregates and other proteins, and at various concentrations ranging preferably from about 0.5 mg/ml to about 20 mg/ml.

The dose to be administered is determined by measuring the effect of the anti-p17 antibody on the lessening of those parameters which are indicative of the disease to be treated. By considering the natural clearance of antibodies, the dose can be repeated periodically according to the clinical status of the patient and the degree of HIV replication. When used as prophylaxis, it may be possible to administer short courses of anti-p17 antibodies bimonthly, six-monthly or annually.

Moreover, the antibodies of the invention can be used as specific reagents in an assay for detection of the protein p17 in a sample of a biological material, such as, for example, a sample of tissue culture or cell culture fluid or a sample of a biological material taken from a patient.

This antigen detection assay can be based on any conventional technique, such as competitive or capture immuno assay (RIA, ELISA, Western blot, TR-FIA etc). To perform competitive immuno assays, the natural or recombinant protein p17 or one or more of the polypeptides based on the neutralizing epitope of the protein p17 according to the present invention can be used. They can be conjugated with markers such as, for example, enzymes for ELISA techniques, radioactive materials for RIA techniques, or fluorescent molecules for TR-FIA techniques or other immunofluorescent techniques. The detection of the antigen can be obtained by immunofluorescence, flow cytometry or other techniques known in the art.

The examples which follow are provided by way of illustration and are not intended to limit in any way the scope of the present invention.

EXAMPLES

Example 1

Production of Recombinant p17

The coding sequence of the protein p17 of the BH-10 isolate of HIV-1 (amino acid 1-32, Ratner, L., W. Haseltine, R. Patarca, K. J. Livak, B. Starcich, S. F. Josephs, E. R. Doran, J. A. Rafalski, E. A. Whitehoren, K. Baumeister, L. Ivanoff, S. R. Petteway, M. L. Pearson, J. a. Lautenberger, T. S. Papas, J. Ghrayeb, N. T. Chang, R. C. Gallo, and F. Wong-Staal, 1985, Nature 313:277-284) was amplified by means of PCR and cloned in the BamH1 site of the pGEX-2T plasmid (Pharmacia, Uppsala, Sweden) which allowed its fusion with the $NH_2$-terminal end of the glutathione S-transferase enzyme (GST).

The primers and the oligonucleotide sequences utilized were based on the entry HIVBH10 of the GenBank data bank, which corresponds to the complete genome of the isolate BH-10 of HIV-1. The correct sequence of the cloned p17 gene was confirmed using the sequencing primers pGEX (Pharmacia), an automatic DNA sequencer (ABI PRISM 310; Perkin Elmer, Foster City, Calif.) and the ABI PRISM equipment Big Dye Terminator Cycle Sequencing Ready Reaction Kit with AmpliTaq DNA polymerase FS (Perkin Elmer).

The GST fusion proteins were expressed in *Escherichia coli* and purified utilizing 4B sepharose glutathione beads (Pharmacia). The viral protein was cut by GST whilst it was still bound to agarose-glutathione beads, as described in Gearing, D. P., N. A. Nicola, D. Metcalf, S. Foote, T. A. Willson, N. M. Gough, and R. L. Williams, 1989, BioTechnology 7:1157-1161).

The protein p17 was further purified by means of reverse phase FPLC, reaching a purity of greater than 98%.

The absence of contamination by endotoxins in the preparation of recombinant p17 of HIV-1 (<0.1 units of endotoxin/ml) was verified with the test based on the *Limulus* amebocytes (Whitaker BioProducts, Inc, Walkersville, Md., USA). The purified p17 of HIV-1 was also biotinylated utilizing AH-NHS-biotin (SPA, Milan, Italy) according to the producers' instructions.

Example 2

Culture of Peripheral Mononucleated Blood Cells (PBMC)

The PBMCs were isolated by Ficoll-Hypaque density gradient (Pharmacia) from heparinated blood just collected from healthy subjects. The cells were seeded into 96-well culture plates with U-bottom (Nunc, Roskild, Denmark) at a density of $10^6$ cells/ml and were cultivated for the indicated number of days at 37° C. in RPMI-1640 medium (Sigma, St. Louis, Mo.) supplement with 10% of human AB serum inactivated by heating (Sigma), penicillin 100 U/ml and streptomycin complete medium 100 µg/ml.

Example 3

Effect of p17 on the Secretion of TNF-α and INF-γ by PBMC Stimulated with IL-2

To evaluate if p17 can influence the production of some pro-inflammatory cytokines, that is to say TNF-α and INF-γ, which is well known to create an environment more suitable for the replication of HIV-1, a series of experiments were conducted to measure the secretion of these cytokines by PBMCs in a culture stimulated with IL-2 in the absence and in the presence of p17. Various doses of IL-2 from 2.5 to 100 U/ml were tested.

In all the subjects analysed, a dose of 20 U/ml gave a consistent induction of the secretion both of TNF-α and INF-γ in the supernatant of the PBMC culture. The addition of p17 at different doses increased the production of these cytokines by the PBMCs treated with IL-2. The maximum increase was noted at a concentration of p17 of 50 ng/ml, although the p17 was biologically active at low concentrations down to 5 ng/ml. At a concentration of p17 of 50 ng/ml the increase was more pronounced for TNF-α (from 36 to more than 100%) than for INF-γ (from 29 to 50%).

No increase in the production of cytokines by p17 was observed on non stimulated PBMC cultures.

Example 4

Reversal of the Inhibition Induced by IL-4 on the Production of TNF-α and INF-γ by p17

The addition of IL-4 to cultures of PBMCs stimulated with IL-2 reduced both the production of INF-γ and that of TNF-α. The reduction in secretion of INF-γ was between 62 and 83%, whilst the reduction in secretion of TNF-α was between 68 and 84%.

To verify if p17 is able to counteract the inhibitory effects of IL-4, the viral protein was added to PBMCs at the beginning of the culture simultaneously with IL-2 and IL-4.

After 72 hours in culture the supernatants were collected and analyzed for the secretion of TNF-α and INF-γ.

In all the experiments performed the results obtained show that p17 is able to restore the capacity of PBMC to produce TNFα and INFγ, with a recovery respectively of 88-100% and 77-89%.

Example 5

Test for the Binding of p17 to a Specific Cell Receptor

To establish if the activity of p17 is due to interaction with a receptor expressed on the target cell, the viral protein was conjugated with biotine and caused to react with PBMCs just isolated from healthy subjects or stimulated for 48 hours with phytohemoagglutinin (PHA).

The p17 was then identified on the cell surface by the use of streptavidin marked with phycoerythrin by flow cytometry.

The experiment was conducted in the following manner. The PBMCs were either stimulated or not for two days with PHA at a concentration of 5 µg/ml and then incubated for 30 minutes on ice with different quantities of biotinylated p17 ranging between 50 ng/ml and 1.6 µg/ml. The PBMCs were washed twice with PBS and incubated for 30 minutes in ice with a suitable quantity of streptavidin conjugated with phycoerythrin (Becton Dickinson, San Jose, Calif.) diluted in PBS containing 2% of foetal calf serum (FCS). In some experiments the cells were also coloured with anti CD-4, anti CD-8, anti CD-16 or anti CD-19 monoclonal antibodies conjugated with isothiocyanate Fluorescein (FITC) (Becton Dickinson). To evaluate the background fluorescence, antibody conjugates for the control of the isotype IgG (Becton Dickinson) were included. The cells were then washed twice with PBS containing 26 of FCS and 0.2% of $NaN_3$ and analyzed on a FACSCalibur flow cytometer (Becton Dickinson). The analysis was performed by utilizing the CellQuest software (Becton Dickinson).

The results obtained on PBMCs freshly isolated from a patient show that the p17 does not bind the T CD-4$^+$ and the T CD-8$^+$ lymphocytes, nor the NK cells (CD-16$^+$), but that, on the other hand, it is present on the surface of the majority of the B lymphocytes (CD-19$^+$). On the contrary, when stimulated, the T CD-4$^+$ and T CD-8$^+$ lymphocytes and NK lymphocytes acquire the capacity of binding the p17.

The data demonstrate that there is a receptor for p17 of HIV on circulating lymphocytes and that it is constitutively expressed on B lymphocytes whilst it is inducibly expressed on the surface of T lymphocytes.

Example 6

Production of Anti-p17 Neutralizing Monoclonal Antibodies

Female Balb/c mice were primed with 100 µg of p17 of example 1 emulsified in complete Freund's adjuvant and boosted at 15 day intervals with 100 µg of protein in incomplete adjuvant. After three days from booster No. 4 the spleens were removed for cell fusion. The fusion protocol, which envisages the use of NS-0 mouse myeloma cells in the presence of polyethylene glycol at 50%, was described in Horan Hand, P., A. Thor, D. Wunderlich, R. Muraro, A. Caruso, and J. Schlom, 1984, Proc. Natl. Acad. Sci. USA 81:5227-5231.

The specificity of the antibodies was determined by means of ELISA and Western blot. In brief, 96-well microtitration plates made of polystyrene were coated with p17 (0.25 µg/well) in carbonate buffer. After washing with PBS containing 0.05% of Tween-20 (v/v), the supernatant of the hybridoma tissue culture was added to the wells coated with p17. After one hour of incubation at 37° C. and washing, the binding of the p17 monoclonal antibodies was detected using anti-mouse IgG goat antibodies conjugated with horseradish peroxydase (Deco, Glostra, Denmark) followed by the addition of o-phenylene diamine as substrate for the calorimetric reaction.

The reactivity of the monoclonal antibodies with native p17 was evaluated by Western blot analysis utilizing a commercial kit for Western blot analysis of HIV-1 (Sanofi Diagnostic Pasteur, Marnes La Coquette, France).

Example 7

Test for Neutralization of the Biological Activity of p17 of HIV-1

It was checked if the anti-p17 monoclonal antibodies obtained in Example 6 could influence the biological activity of p17 and the interaction of the protein with its cellular receptor expressed on T and B lymphocytes.

The PBMCs were cultivated in triplicate in 96-well plates with U-bottoms in complete medium with IL-2 (at a concentration of 20 U/ml) in the presence or in the absence of different concentrations of purified recombinant p17 (ranging between 2.5 and 100 ng/ml). The inhibition of the secretions of TNF-α and INF-γ was obtained by adding IL-4 (20 ng/ml) to the cells stimulated with IL-2. At the beginning of the culture the anti-p17 antibodies were added to the cells in concentrations ranging between 0.5 and 10 µg/ml. After three days of cellular activation the culture supernatants were collected and tested for the presence of TNF-α and INF-γ.

Anti-p17 antibodies in the above-indicated concentrations were also utilized to block the binding of p17 with the cellular receptor expressed by the T and B lymphocytes. The capacity of the antibodies to block the p17/receptor binding was evaluated by means of flow cytometry.

Among the various antibodies obtained in Example 6, only one of them denominated MBS-3 was able to block the effects of p17 on the secretion of pro-inflammatory cytokines. In fact, the PBMC cells stimulated with IL-2 and p17 reduced the production of INF-γ and TNF-α to levels comparable with those obtained in cultures stimulated with IL-2 only when the MBS-3 monoclonal antibody was added to the culture at the beginning of stimulation with the mitogen (data not shown).

The addition of MBS-3 to cultures stimulated with IL-2 plus IL-4 and p17 completely blocked the capacity of the viral protein to reverse the inhibitory activity of IL-4.

Other anti-p17 monoclonal antibodies, and among these one in particular denominated as MK-1, did not show any capacity for neutralization. Moreover, the addition of MBS-3 at the beginning of stimulation with the mitogen did not interfere, in the absence of p17, with the synthesis of the pro-inflammatory cytokines and with the inhibitory IL-4. Finally, MBS-3 (but not MK-1) completely blocked the binding of p17 with its receptor in a dose-dependent manner.

Example 8

Epitope Mapping

The anti-p17 neutralizing monoclonal antibody MBS-3 was characterized by binding to specific epitopes of p17 by means of the epitope mapping technique.

On the basis of the known sequence of p17 of the HB10 strain of the HIV-1, 62 peptides of 10 amino acids in length were synthesized. These peptides were representative of the entire length of p17 and overlapped one another with a shift along the p17 molecule of two amino acids.

As a positive control for the synthesis of the peptides and for the reactivity of the antibodies the polypeptide EAEN-LKKYFN (SEQ ID NO: 4: one letter code) of INF-γ was also synthesized, which is recognized by the monoclonal antibody IGMB-15 (Caruso A., L. Tiberio, C. De rango, C. Nonfanti, G. Flamminio, G. Gribaudo, E, Monti, E. Viani, N. Macna, G. Garotta, S. Landolfo, A. Balsrai, and A. Turano, 1993, J. Immunol. 150: 1029-1035).

The peptides were synthesized utilizing a SPOT Synthesis kit (Genosys Biotechnologies, Pampisfors, Great Britain) on a cell membrane of 8×12 cm in area derivatized with a dimer of β-alanine having exposed amino groups ($NH_2$). The reactivity of the monoclonal antibodies against the peptides was evaluated according to the supplier's instructions.

The binding region of MBS-3 was then identified in the sequence included between positions 9 and 22 of p17 (SEQ ID NO: 2). The same peptide was also recognized by another two anti-p17 neutralizing antibodies in an ELISA test in solid phase, whilst other non-neutralizing anti-p17 antibodies did not recognize it.

Moreover, in a competitive ELISA test the above-indicated peptide was efficacious in displacing the binding of the antibody MBS-3 to p17 absorbed in solid phase.

Example 9

Affinity Chromatography of Anti-p17 Antibodies 2 mg of peptide having the amino acid sequence SEQ ID NO:2 with an additional residue of lysine (Lys) at its C-terminal were bound with 2 ml of Sulfolink coupling gel (Pierce, Rockford, Ill.) following the standard protocol recommended by Pierce. The affinity column was connected to an FPLC apparatus (Pharmacia) and equilibrated with phosphate buffered saline (PBS). Hybridoma supernatants containing the anti-p17 monoclonal antibodies MBS-3 were applied to the column at a flow rate of 0.1 ml/min and the bound antibodies were eluted at the same flow rate with glycine 0.1M, pH 3.0. Eluted antibodies were found to specifically recognize the protein p17 in Western blot analysis (data not shown).

The invention claimed is:

1. An isolated polypeptide capable of evoking an anti-p17 antibody that inhibits the proinflammatory biological function of HIV p17 protein consisting of an amino acid sequence NH$_2$-X$^1$-Gly-X$^2$-X$^3$-Leu-Asp-X$^4$-Trp-Glu-X$^5$-Ile-X$^6$-Leu-Arg-COOH (SEQ ID NO: 1), wherein X$^1$ is an amino acid residue selected from Ser and Arg, X$^2$ is an amino acid residue selected from Gly, Glu and Ser; X$^3$ is an amino acid residue selected from Glu, Lys, Asp and Arg; $X^4$ is an amino acid residue selected from Arg, Ala, Lys, Thr, Ser, Glu, Asp and Gln; $X^5$ is an amino acid residue selected from Lys, Arg and Ser; and $X^6$ is an amino acid residue selected from Arg and Gln.

2. A polypeptide according to claim 1, in which said amino acid sequence is $NH_2$-Ser-Gly-Gly-Glu-Leu-Asp-Arg-Trp-Glu-Lys-Ile-Arg-Leu-Arg-COOH (SEQ ID NO: 2).

3. A polypeptide according to claim 1, in which a second amino acid sequence capable of increasing the solubility of the polypeptide is directly bound to the amino acid residue in the carboxyterminal position of SEQ ID NO:1 or SEQ ID NO: 2.

4. A polypeptide according to claim 3, in which the second amino acid sequence is -Pro-Gly-Gly-Lys-Lys-Lys-Tyr-Lys-COOH (SEQ ID NO:3).

5. A polypeptide according to claim 1, which is conjugated with a carrier.

6. A polypeptide according to claim 5, which is conjugated with a carrier through an additional residue of cysteine (Cys) or an additional dipeptide -Nleu-Cys in the carboxyterminal position.

7. A polypeptide according to claim 1, which is in the form of a branched peptide.

8. An immunogenic composition comprising a polypeptide according to claim 1 and a pharmaceutically acceptable vehicle.

* * * * *

SEQUENCE LISTING

```
<160> NUMBER OF SEQ ID NOS: 4

<210> SEQ ID NO 1
<211> LENGTH: 14
<212> TYPE: PRT
<213> ORGANISM: HIV
<220> FEATURE:
<221> NAME/KEY: MISC_FEATURE
<222> LOCATION: (1)..(1)
<223> OTHER INFORMATION: Xaa is selected from Ser and Arg
<220> FEATURE:
<221> NAME/KEY: MISC_FEATURE
<222> LOCATION: (3)..(3)
<223> OTHER INFORMATION: Xaa is selected from Gly, Glu and Ser
<220> FEATURE:
<221> NAME/KEY: MISC_FEATURE
<222> LOCATION: (4)..(4)
<223> OTHER INFORMATION: Xaa is selected from Glu, Lys, Asp and Arg
<220> FEATURE:
<221> NAME/KEY: MISC_FEATURE
<222> LOCATION: (7)..(7)
<223> OTHER INFORMATION: Xaa is selected from Arg, Ala, Lys, Thr, Ser,
      Glu, Asp and Gln
<220> FEATURE:
<221> NAME/KEY: MISC_FEATURE
<222> LOCATION: (10)..(10)
<223> OTHER INFORMATION: Xaa is selected from Lys, Arg and Ser
<220> FEATURE:
<221> NAME/KEY: MISC_FEATURE
<222> LOCATION: (12)..(12)
<223> OTHER INFORMATION: Xaa is selected from Arg and Gln

<400> SEQUENCE: 1

Xaa Gly Xaa Xaa Leu Asp Xaa Trp Glu Xaa Ile Xaa Leu Arg
1               5                   10

<210> SEQ ID NO 2
<211> LENGTH: 14
<212> TYPE: PRT
<213> ORGANISM: HIV

<400> SEQUENCE: 2

Ser Gly Gly Glu Leu Asp Arg Trp Glu Lys Ile Arg Leu Arg
1               5                   10

<210> SEQ ID NO 3
<211> LENGTH: 8
<212> TYPE: PRT
<213> ORGANISM: HIV

<400> SEQUENCE: 3

Pro Gly Gly Lys Lys Lys Tyr Lys
1               5

<210> SEQ ID NO 4
<211> LENGTH: 10
<212> TYPE: PRT
<213> ORGANISM: HIV

<400> SEQUENCE: 4

Glu Ala Glu Asn Leu Lys Lys Tyr Phe Asn
1               5                   10
```